United States Patent [19]

Bley

[11] Patent Number: 5,250,020
[45] Date of Patent: Oct. 5, 1993

[54] UNITARY INFLATABLE PENILE PROSTHESIS

[75] Inventor: Robert Bley, Goleta, Calif.

[73] Assignee: Mentor Corporation, Santa Barbara, Calif.

[21] Appl. No.: 758,738

[22] Filed: Sep. 12, 1991

[51] Int. Cl.$^5$ .............................................. A61F 2/26
[52] U.S. Cl. ...................................................... 600/40
[58] Field of Search ........................... 600/40; 206/438

[56] References Cited

U.S. PATENT DOCUMENTS

| | | | |
|---|---|---|---|
| 3,954,102 | 5/1976 | Buuck | 600/40 |
| 4,596,242 | 6/1986 | Fischell | 600/40 |
| 4,597,765 | 7/1986 | Klatt | 206/438 |
| 5,101,813 | 4/1992 | Trick | 600/40 |

*Primary Examiner*—Cary E. O'Connor
*Attorney, Agent, or Firm*—Blakely, Sokoloff, Taylor & Zafman

[57] ABSTRACT

A factory preassembled, preferably partially prefilled three piece penile prosthesis that can be implanted in a patient as one pre-assembled unit and filled without any required further connection or purging of air. The prosthesis has a pair of inflatable cylinders that can be implanted into the corpora cavernosa regions of the penis, the inflatable cylinders preferably being attached to a solid rear portion to which the various tubing is connected. The prosthesis also has a reservoir for implantation into the abdomen, a pump for implantation into the scrotum for transferring fluid from the reservoir into the cylinders, and a controllable valve associated with the pump for retaining the fluid within the cylinders and for controllably allowing it to escape from the cylinders back into the reservoir when desired. When fluid is pumped into the cylinders, the cylinders are inflated to to encourage the penis to an erect position. When the fluid is subsequently released from the cylinders, the cylinders deflate to allow the penis to return to a relaxed position. The volume of fluid within the preoperative prosthesis assembly is such that sufficient fluid may be readily displaced from the reservoir into the pump and cylinders to allow the reservoir to be inserted into the pelvic cavity of a patient without disconnecting the pump and cylinders. An alternate embodiment contemplates an unfilled prosthesis assembly, retaining the advantages of a preassembled unit in implantation time required and elimination of the potential for eventual connector failure.

23 Claims, 4 Drawing Sheets

UNITARY INFLATABLE PENILE PROSTHESIS

BACKGROUND OF THE INVENTION

1. Field of the Invention

The present invention relates to a penile prosthesis for erecting a male penis, and methods of implanting the same.

2. Description of Related Art

A penile prosthesis is typically installed in a patient to remedy erectile impotence. One common type of penile prosthesis, termed an inflatable penile prosthesis or IPP, is provided with three separate functional elements, namely a single cylinder or more commonly a pair of inflatable cylinders for insertion into the corpus cavernosa regions of the penis, a reservoir for disposition in the abdominal cavity and a pump for disposition in the scrotum, together with tubing which is trimmed to length and used to interconnect all of the elements at the time of surgery. Specifically, there is typically one tube for connection from the pump to each cylinder and one tube for connection from the pump to the reservoir. In operation after implantation, the cylinders are filled with a fluid from the reservoir that inflates the cylinders, thereby causing the penis to erect. When fluid is drained from the cylinders back to the reservoir, the cylinders and penis return to a relaxed position (flacid state). For inflation of the cylinders, the pump is manually activated to add fluid from the reservoir to the cylinders, with a valve being provided with the pump to permit and restrict the flow of fluid to and from the cylinders. Such devices are described in various prior art references such as U.S. Pat. Nos. 3,855,122, 3,954,102, 4,009,711, 4,201,202, 4,235,227 and 4,318,396. (The foregoing types of prostheses are commonly referred to as "three piece" penile prostheses, which terminology is preserved in the description of the present invention to distinguish over "two piece" penile prostheses wherein the pump also functions as the reservoir, though as shall be seen, the present invention does not have separate "pieces" but rather is one integrated assembly requiring no further interconnection at the time of implantation, in a preferred embodiment, a partially prefilled assembly substantially free of air and ready for implantation and final filling.)

The reservoir is usually a flexible bag for volume expansion and contraction primarily through shape changes as opposed to material stretching. For one method of implantation, the reservoir is typically inserted through the inguinal ring and implanted into the abdominal cavity behind the muscles of the lower abdomen of the patient. In that regard, the reservoir is generally too large to be pushed through the inguinal ring if it is filled with the intended working fluid, so the reservoir is usually substantially deflated before implantation.

Present surgical procedures include implanting the cylinders in the penis and filling them to test the resultant erection, and then emptying the cylinders, implanting an empty or substantially empty reservoir into the pelvic cavity, filling the reservoir with the filling fluid, implanting the pump and then connecting all of the elements together with the tubing. In connecting the tubing from the reservoir to the pump, an extra long length of tubing is generally supplied. The tubing must be clamped off and trimmed to the proper length for the individual patient. The pump is then implanted into the scrotum and the cylinders are inserted into the penis pendulum.

As indicated above, the reservoir must be devoid of most fluid in order to be implanted through the inguinal ring, and the pump, cylinders and tubing do not have sufficient volume to retain all of the fluid needed in the system. Therefore, the prior art inflatable penile implant systems must remain unconnected, and are typically unfilled until after the reservoir is installed. This is because a filled reservoir, if first connected, cannot be sufficiently temporarily drained into the remaining components for implantation into a patient. Thus, in order to properly install a prior art IPP of this type, it is necessary to first trim the tubing to length and fill the reservoir to purge most air therefrom, then to substantially empty the reservoir and clamp the tubing without reintroducing air, then to pass the reservoir through the inguinal ring and into the abdominal cavity, and then to fill the reservoir through the unconnected tubing before the remainder of the device is installed and connected together. The air purging, etc. of the reservoir prior to its implantation and its refilling after implantation in the abdominal cavity is time consuming, thereby not only increasing implantation time, but also the cost and risk associated with implantation.

Another problem with prior art penile implants of this type is that the attachment of the pump and cylinder to the reservoir often traps air within the system. Excessive air is undesirable because it is compressible, will leak through a valve at a much higher rate than the intended fluid and has other undesirable effects such as possibly creating noise when being pumped with the fluid. Air also usually is present in lieu of an approximately equal amount of additional working fluid, thereby reducing the total amount of the working fluid present, potentially below the minimum required for proper operation of the system. Since the air will slowly disperse by osmosis through the implant wall over a period of time, an implant that works satisfactorily immediately after implantation on the combination of the intended working fluid and air functioning for the time being as additional working fluid may not work properly after a period of time. Thus the presence of air should be minimized. To purge the assembled prosthesis of air, a small volume of fluid is added to the system. The surgeon must then wait while the trapped air separates from the fluid. A needle is then inserted into the pocket of air and the air is withdrawn from the system. This procedure is repeated until all visible air is removed. The pump is then implanted into the scrotum and the cylinder is inserted into the penis pendulum. The assembly of the prosthesis and the subsequent purging of air are also time consuming steps that extend the length of surgery. Additionally, with the prior art methods, it is difficult to insure that all of the air is removed from the prosthesis assembly as desired.

The interconnection of the components of the prior art penile implants is also problematic. (Connectors such as those described in U.S. Pat. Nos. 4,537,183 have been used in the past for this purpose.) The tubes must connect the components together as described above, but this interconnection is time consuming and labor intensive, thereby also increasing the time required for the operation and the associated risks of extending the time of the operation. Further, the connectors present a step change from the flexibility of the tubes, creating stress concentrations at the point of attachment of the tubes to the connectors and providing a possible source of failure over a period of time because of repeated flexing at these points. Elimination of the connectors would eliminate this potential source of failure, as a length of flexible tubing integral with the same adjacent tubing is itself extremely reliable.

In U.S. Pat. Nos. 4,597,765, a method and apparatus for packaging a fluid filled prosthesis is disclosed which allows the prefilling of a prosthesis at the factory and shipment and storage of the prosthesis in the fluid filled state, despite the tendency for fluid migration through the walls of the device, by establishing mass transfer equilibrium within the package. The method disclosed works well for two piece penile prostheses, particularly those adversely effected by slight fluid loss, but is not applicable to three piece prostheses, as the reservoir of a prefilled three piece prosthesis generally cannot be adequately collapsed for implantation purposes.

It would therefore be desirable to have a penile prosthesis and a method of installing the same that would make it easier and faster to implant, and which would eliminate the connectors and thus a potential source of deterioration and failure in the operating system, thereby greatly reducing surgery time and failure after some period of use, to the advantage of the patient and surgeon alike.

SUMMARY OF THE INVENTION

The present invention is a factory preassembled, preferably partially prefilled three piece penile prosthesis that can be implanted in a patient as one pre-assembled unit and filled without any required further connection or purging of air. The prosthesis has a pair of inflatable cylinders that can be implanted into the corpora cavernosa regions of the penis, the inflatable cylinders preferably being attached to a solid rear portion to which the various tubing is connected. The prosthesis also has a reservoir for implantation into the abdomen, a pump for implantation into the scrotum for transferring fluid from the reservoir into the cylinders, and a controllable valve associated with the pump for retaining the fluid within the cylinders and for controllably allowing it to escape from the cylinders back into the reservoir when desired. When fluid is pumped into the cylinders, the cylinders are inflated to encourage the penis to an erect position. When the fluid is subsequently released from the cylinders, the cylinders deflate to allow the penis to return to a relaxed position. The volume of fluid within the preoperative prosthesis assembly is such that sufficient fluid may be readily displaced from the reservoir into the pump and cylinders to allow the reservoir to be inserted into the pelvic cavity of a patient without disconnecting the pump and cylinders.

Accordingly, a filling port is provided on the prosthesis, preferably in the rear portion, though on the pump or in the associated tubing if desired, to facilitate filling of the prosthesis to its operating volume after the reservoir is implanted. A resealable filling port is preferably provided for easy and fast filling with minimum opportunity for leakage.

The assembled prosthesis is installed by first deflating the reservoir by displacing most of the fluid from the reservoir to the pump and cylinders and inserting the collapsed reservoir into the pelvic cavity of the patient. The assembly is then injected, typically with a predetermined amount of fluid, until the prosthesis is filled with an operating volume of fluid. The cylinders and pump are subsequently implanted into the penis and scrotum, respectively. There is no need for the surgeon to connect the various components, or purge air therefrom as was required in the prior art, as this has already been done under closely controlled factory conditions.

Therefore it is an object of this invention to provide a three piece penile prosthesis that can be installed into a patient as a single unit.

It is also an object of this invention to provide a three piece penile prosthesis that can be implanted and used without having to purge the system of air at the time of implantation.

It is also an object of the present invention to provide a three piece penile prosthesis that can be packaged and shipped in a pre-interconnected state so that no connection or assembly is required upon implantation.

It is also an object of the present invention to provide a three piece penile prosthesis that can be filled without having to connect or disconnect any of the associated elements, including the tubing.

It is another object of the present invention to provide a three piece penile prosthesis containing a volume of operating fluid which can be all or mostly contained within the inflatable cylinders, pump and associated tubing such that the system need not be disconnected in order to implant the reservoir.

It is yet another object of the present invention to provide a fully assembled, partially fluid filled three piece penile prosthesis which is fillable without any disassembly.

In another embodiment, it is yet another object of the present invention to provide a fully assembled, unfilled three piece penile prosthesis, the same being free of the usual connectors and thus free of a recognized and substantial source of failures of such implants, and further being more quickly purged of most air and readily implanted without the time consuming assembly at the time of implantation characteristic of prior art three piece penile implants.

BRIEF DESCRIPTION OF THE DRAWINGS

The objects and advantages of the present invention will become more readily apparent to those skilled in the art after reviewing the following detailed description and accompanying drawings, wherein.

DETAILED DESCRIPTION OF THE INVENTION

Figure 1:
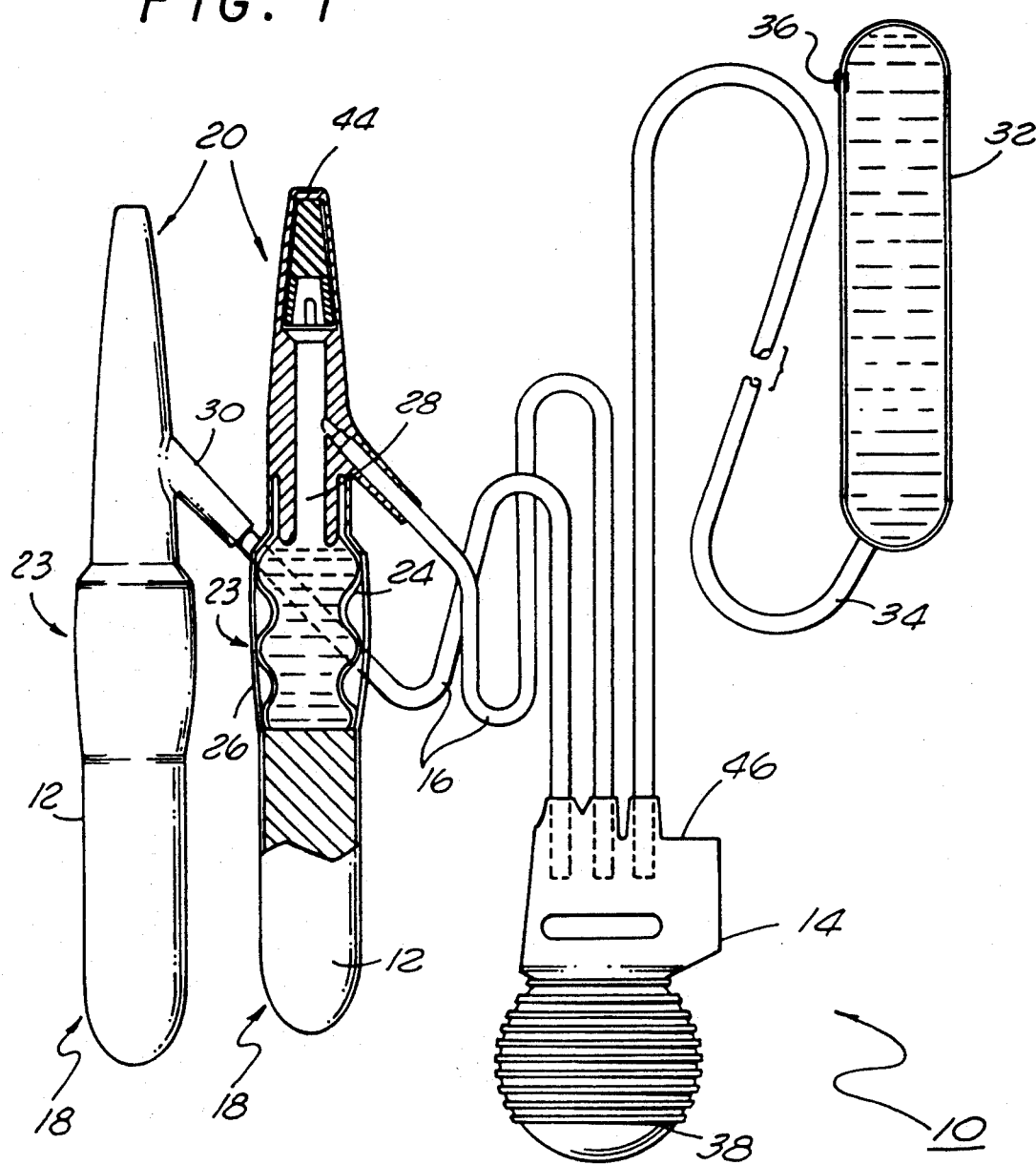
FIG. 1 is a side view of a penile prosthesis assembly of the present invention.

First referring to FIG. 1, a penile prosthesis assembly 10 in accordance with the present invention may be seen. The assembly 10 has two inflatable cylinders 12, each part of a cylinder assembly 18 and connected to a pump 14 by a pair of first tubes 16. Although two cylinder assemblies 18 are shown, it is to be understood that only one cylinder 12 may be used if desired.

The portion of the assembly implanted in the penis is the cylinder assemblies 18, which comprise an inflatable cylinder 12 and a base portion 20. In the preferred embodiment, between each cylinder 12 and the respective base portion 20 is an extension member 23 having a bellows 24 therein constructed to be extendable with the addition of a fluid to the interior thereof. A distensible sleeve 26 is disposed over the bellows 24 and attaches the base portion 20 to the cylinder 12 so that when fluid is added to the bellows 24 to extend the same, the sleeve 26 is itself stretched into an extended position. Subsequent release of a valve holding the fluid in the bellows allows the same to retract, with the stretched sleeve 26 helping to expel fluid therefrom and pull the cylinder 12 back to the relaxed position. This sheath and bellows inflatable cylinder, which is one form of inflatable cylinder which may be used in the present invention, is described in detail in copending U.S. patent application, Ser. No. 07/733,426.

Fluid communication between the first tubes 16 and inflatable cylinder 18 is established by an opening 28 located in the base portion 20, with stem 30 providing a means of attachment for the tube 16. The pump 14 is connected to the reservoir 32 by a second tube 34, which is continuous and without any connectors. The reservoir 32 is made from a flexible bag material so that the volume of the reservoir 32 can increase and decrease as required. While the reservoir 32 may have a port 36 which provides a point of entry for a needle that can supply fluid to the reservoir 32, the filling port for the system is elsewhere, such as filling port 44 in the base portion 20 of the cylinder assemblies, or alternatively for instance, filling port 46 in the pump housing 38. (Typically both ports will not be used on any one prosthesis, but could be if desired.) The filling port is preferably disposed in the base portion 20 because that portion is of substantial size and thickness already and not subject to substantial flexing in use, so that a filling port may be integrated into that region in a manner that is relatively undetectable by feel, thereby not constituting a possible source of irritation or discomfort. As will be more fully described with respect to FIGS. 6 and 7, the filling port can have a raised or lowered ring or other shape to function as a better target for the surgeon, though the preferred method of implantation of the present invention envisions final filling of the prosthesis before implantation of the cylinder assemblies when visibility, etc. are at a maximum. Of course the filling port may be provided with a needle guard for safety purposes, as is well known in the art, and may be of any of a variety of types which are well known in the art, including a compression port if desired.

The pump 14 and valve assembly 42 are constructed so that fluid may be supplied to the cylinders 12 by squeezing and releasing the pump housing 38 one or more times. The valve is constructed in the form of a release valve, as is known in the art, allowing fluid to return from the cylinder assemblies to the reservoir upon manual squeezing of the valve assembly 14.

The entire assembly is provided preassembled, purged of most air and partially filled with the intended working fluid. The fluid is preferably isotonic, and may include but is not limited to a saline solution or PVP.

The volume of fluid within the assembly 10 is such that most of the fluid may be forced into the cylinders, either by successive operation of the pump or by simultaneous squeezing of the reservoir and the valve assembly, so that the reservoir 32 will be sufficiently deflated to be inserted into the pelvic cavity of a patient. The volume of the prefill fluid will depend on the size of the reservoir, pump, cylinders and tubing utilized for the particular patient, though in general the volume of prefill fluid in the system may be from somewhat less than the fluid capacity of the pump, cylinders and tubing, to somewhat more than the fluid capacity of the pump, cylinders and tubing, as desired. In that regard, a reservoir which has some fluid therein will "hourglass" as it is passed through a small opening, thereby limiting the degree to which it must be emptied for convenient implantation. Thus the amount of prefill fluid is preferably limited on the upper end to an amount which does not encourage overstressing of the cylinders and pump to remove sufficient fluid from the reservoir to allow easy implantation thereof—perhaps 5 cc of fluid left in the reservoir still making the reservoir easily implantable. On the lower end, it is desirable to have sufficient fluid in the system to displace the air while avoiding sharp wrinkles in an overly deflated system, and preferably to have sufficient fluid in the system to allow final filling by a single injection of fluid.

The prosthesis 10 is provided to the surgeon in the assembled, partially filled condition shown and described above. To install the assembly 10, an incision is made at the base of the penis next to the inguinal ring. The incision provides access to the pelvic cavity, scrotum and corpora cavernosa regions of the patient. The reservoir 32 is then substantially deflated by opening the valve 42 and squeezing the contents out of the reservoir, thereby forcing fluid within the reservoir 32 to flow into the rest of the assembly 10. After the reservoir 2 is substantially collapsed, the reservoir is inserted into the pelvic cavity.

Figure 2:
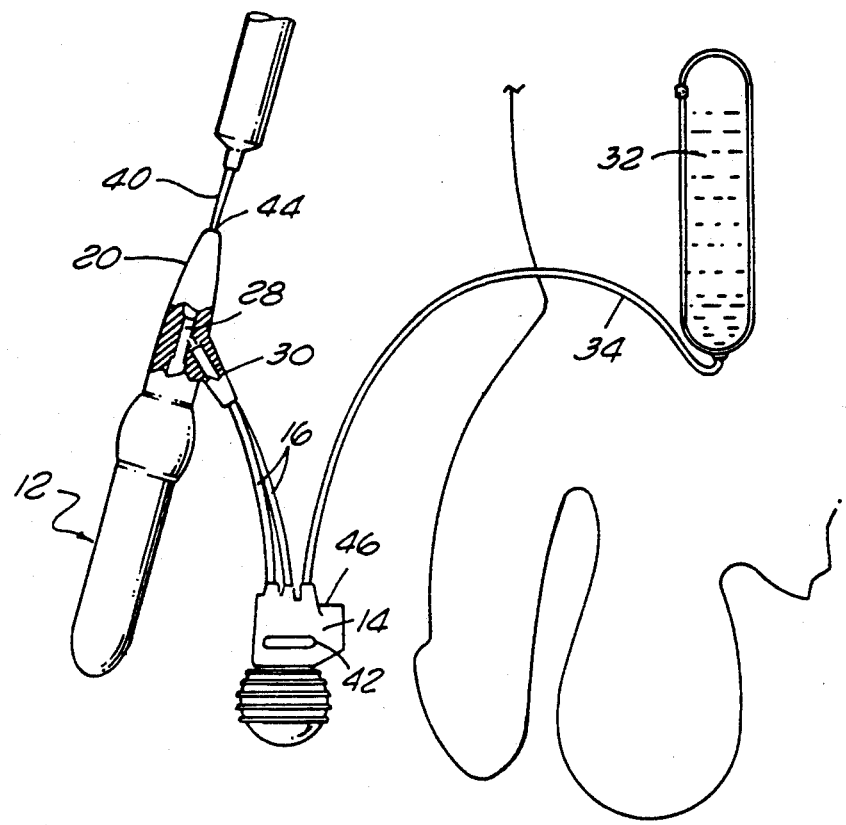
FIG. 2 is a side view of the penile prosthesis assembly of FIG. 1, wherein the reservoir is implanted into the pelvic cavity of a patient and the prosthesis assembly is being injected with additional working fluid.

After the reservoir 32 is implanted into the patient, a filling device, such as syringe 40 as shown in FIG. 2, is used to fill the system to its operable volume, which, as is known in the art, varies depending upon the size of the system and the particular patient. Typically about 40 to 75 cc of fluid is the standard operating volume. The filling port can be almost anywhere in the system as described above, including the pump, the tubing or the base of the cylinders, although it is preferably not in the inflatable part of the cylinders or the reservoir. As stated before, in the presently preferred embodiment, the injection port is in the base portion 20 of the cylinders 12, where material thickness is greater and mechanical cycling is lower than the other components of the assembly 10.

Figure 3:
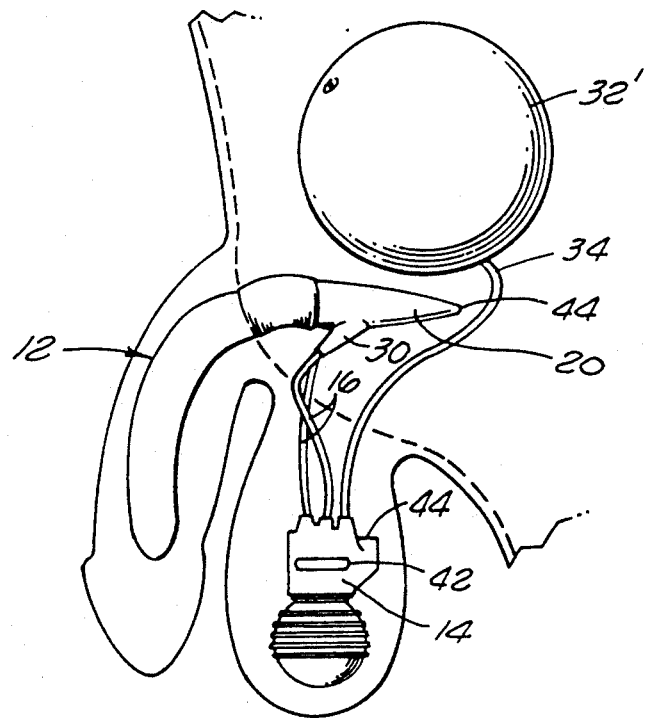
FIG. 3 is a side view of the penile prosthesis assembly of FIG. 2 with the pump of the assembly implanted into the scrotum and the cylinders inserted into the penis of the patient.

Once the assembly is filled to the operating level of fluid, the syringe 40 is removed, the valve squeezed and a substantial part of the fluid allowed to pass back into the reservoir. As shown in FIG. 3, the cylinders 12 and pump 14 are then implanted into the corpora cavernosa regions of the penis and the scrotum, respectively. The installation of the cylinders 12 and pump 14 into these regions can be performed by surgical procedures known in the art. It will be appreciated, however, that utilizing the present invention for implantation, the steps of evacuating air from the system, and of reliably connecting the tubing together as was required in prior art three piece systems are eliminated.

Figure 4:
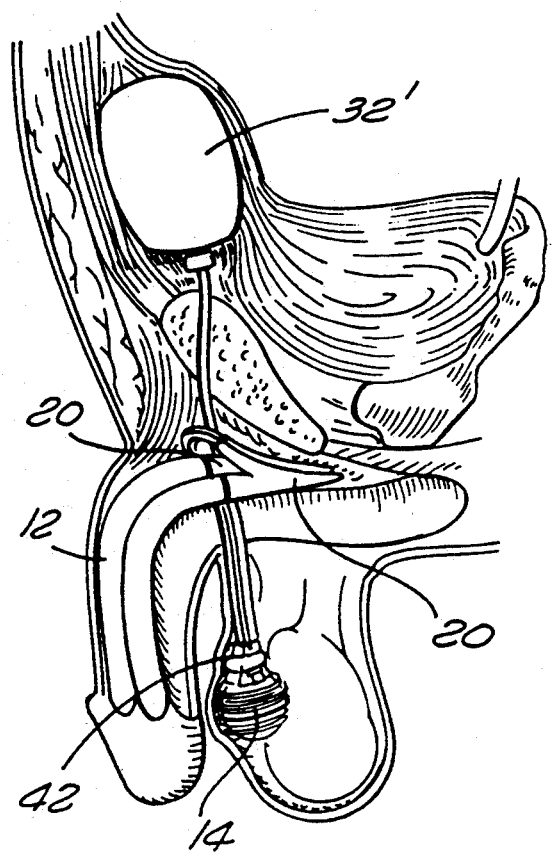
FIG. 4 is an anatomic drawing of the penile prosthesis in a patient in a flaccid condition.
Figure 5:
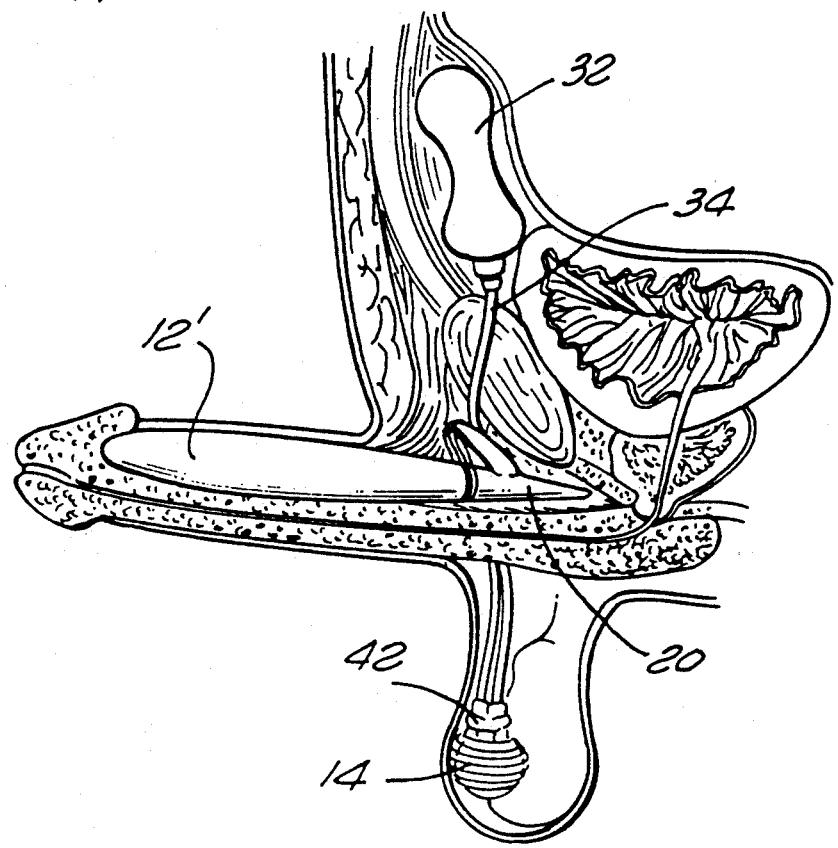
FIG. 5 is an anatomic drawing of the penile prosthesis in a patient in an erect condition.

As shown in FIGS. 4 and 5, the present invention can be used to erect a male penis. The cylinders 12 are disposed within the corpus cavernosa of the penis and are shown in a deflated state in FIG. 4. The cylinders 12' are inflated in FIG. 5. Conversely, the reservoir 32' is inflated in FIG. 4 and reservoir 32 is deflated in FIG. 5.

Figure 6:
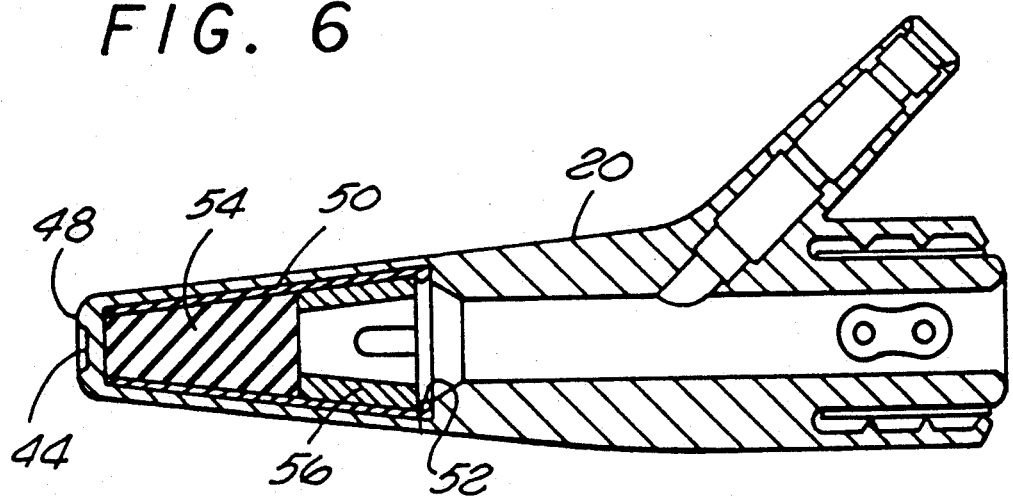
FIG. 6 is a cross section of the base portion 20 of a cylinder illustrating the details of injection port 44 of prior FIGS. 1 through 3.

Now referring to FIG. 6, a cross section of the base portion 20 of a cylinder illustrating the details of injection port 44 of FIGS. 1 through 3 may be seen. The body of base portion is a flexible material, typically a silicon rubber, molded as a single piece, with the injection port location being circumscribed by a ring or raised portion 48 to help the surgeon better locate and confine the location of the tip of the injection needle. Disposed therein is a relatively rigid, substantially conical member 50 having an inward projecting lip 52 at the larger end thereof. A conical slug of soft and flexible silicon rubber 54 is disposed in the end of the conical member 50, and is retained therein under compression by another substantially rigid, hollow conical member 56 slotted from the larger end thereof so as to have sufficient flexibility to pass under lip 52 for assembly purposes, to snap back and to be retained thereby to retain the conical slug of soft and flexible silicon rubber 54 under compression. In this way, the thin end of the body of base portion 20 and the conical slug of soft and flexible silicon rubber 54 may be easily pierced by a needle for injection of working fluid into the prosthesis, with the resulting opening in the conical slug of soft and flexible silicon rubber 54 immediately resealing upon withdrawal of the needle.

Figure 7:
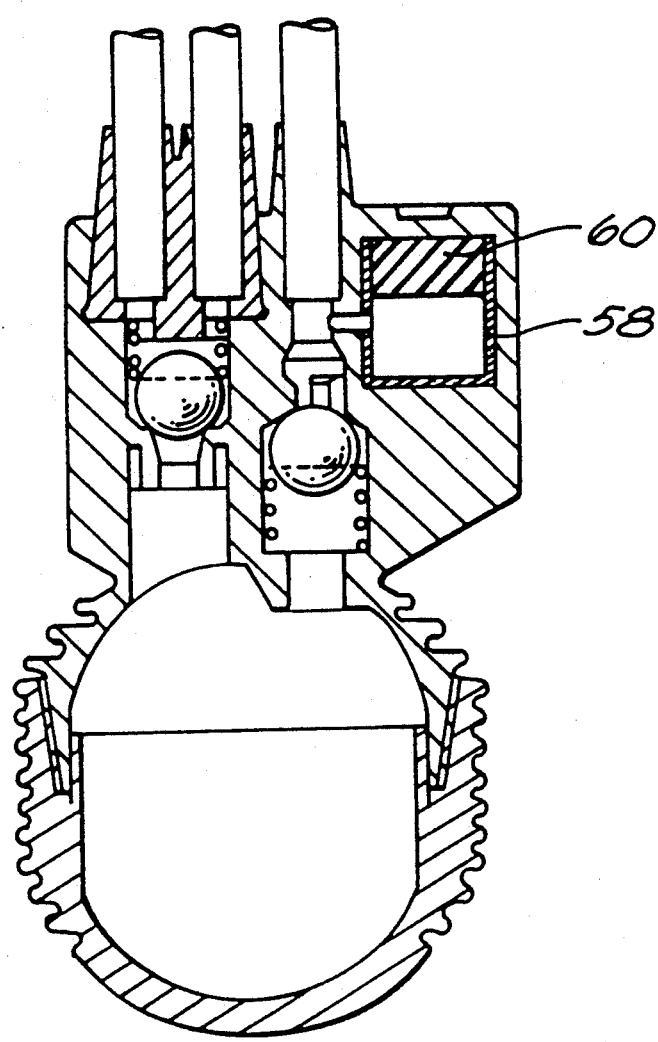
FIG. 7 is a cross section of the pump 14 illustrating the reviewing details of injection port 46 of FIGS. 1 through 3.

Now referring to FIG. 7, a cross section of the pump 14 illustrating the details of one possible design of an injection port 46 on the pump 14 of FIGS. 1 through 3 may be seen. In this injection site, a substantially rigid cup 58 having an opening on the side thereof for fluid communication with the internal parts of the pump is presseed into the flexible body of the pump, and retains a slug of soft and flexible silicon rubber 60 under compression, again to immediately reseal upon withdrawal of the needle. In this injection site, the cup bottom forms a readily detectable stop for the needle, facilitating appropriate placement of the needle before injection.

In the foregoing embodiment, the prosthesis is purged of at least most air and partially prefilled at the time of manufacture, thereby relieving the surgeon of the same rather mechanical tasks at the time of implantation and allowing the same to be done under the less costly and more easily and uniformly controlled factory conditions. However, there are still substantial advantages to be gained by providing to the surgeon a preassembled but not partially prefilled prosthesis, as such a preassembled unit will still eliminate the time required to cut the tubes to length, to assemble connectors, etc., and will more readily facilitate the purging of air from the system, primarily by what is now the simultaneous purging of all "pieces" and the elimination of the opportunity for reintroduction of air into the system as in the prior art when the tubes to the multiple pieces are opened for connection together. Such a nonprefilled assembly also eliminates the possibility of eventual connector failure, a substantial advantage in itself.

While certain exemplary embodiments have been described in detail and one exemplary embodiment shown in the accompanying drawings, it is to be understood that such embodiments are merely illustrative of and not restrictive on the broad invention, and that this invention not be limited to the specific constructions and arrangements shown and described, since various other modifications may occur to those skilled in the art.

I claim:

1. An inflatable penile prosthesis which can be implanted into a pelvic cavity, scrotum and penis of a patient, comprising:
   at least one inflatable cylinder;
   a flexible reservoir adapted to supply fluid to said cylinder;
   a pump constructed to transfer fluid from said reservoir to said cylinder;
   first connecting means connecting said pump and said reservoir;
   second connecting means connecting said pump and said inflatable cylinder;
   a fluid within said cylinder, said pump and said reservoir, said fluid having a volume that allows said reservoir to be inserted into the pelvic cavity of the patient while said pump and said cylinder are attached to said reservoir,
   a port disposed in said inflatable cylinder, wherein said port allows fluid to be injected therein cylinder to increase said fluid volume of said penile prosthesis to an operating volume,
   wherein said cylinder, said reservoir, said pump and said first and second connecting means are provided interconnected.

2. The prosthesis as recited in claim 1, wherein there are two cylinders.

3. The prosthesis as recited in claim 1, wherein said cylinder has a substantially rigid base portion and an inflatable portion.

4. The prosthesis as recited in claim 1, wherein said penile prosthesis contains only as much fluid as can be retained in said inflatable cylinder, said pump and said connecting means.

5. An inflatable penile prosthesis which can be implanted into a pelvic cavity, scrotum and a penis of a patient, comprising a unitary preassembled assembly comprising:
   two inflatable cylinders;
   a flexible reservoir adapted to supply fluid to said cylinders;
   a pump connected to said cylinders by a pair of first tubes and connected to said reservoir by a second tube, said pump being constructed to transfer fluid from said reservoir to said cylinders; and,
   a fluid within said cylinders, said tubes, said pump and said reservoir, said fluid having a volume that allows said reservoir to be inserted into the pelvic cavity of the patient while said pump, said tubes and said cylinders are attached to said reservoir
   wherein said cylinders have a port that allows fluid to be injected therein to increase said fluid volume of said cylinders, said pump and said reservoir to an operating volume.

6. The prosthesis as recited in claim 5, wherein said cylinders have a substantially rigid base portion and an inflatable portion.

7. A method of implanting an inflatable penile prosthesis which can erect a penis of a patient having a pelvic cavity and a scrotum, comprising the steps of: providing a preassembled prosthesis assembly that includes:
   at least one inflatable cylinder;

a flexible reservoir adapted to supply fluid to said cylinder;

a pump connected to said cylinder and said reservoir, said pump being constructed to transfer fluid from said reservoir to said cylinder;

a fluid within said cylinder, said pump and said reservoir, said fluid having a volume that allows said reservoir to be inserted into the pelvic cavity of the patient while said pump and said cylinders are attached to said reservoir;

inserting said reservoir into the pelvic cavity of the patient;

filling said prosthesis assembly with fluid such that said prosthesis assembly has an operating volume of fluid; and implanting said cylinder into the penis and said pump into the scrotum of the patient.

8. The method as recited in claim 7, wherein said prosthesis is filled through a filling port disposed in said penile prosthesis.

9. The method as recited in claim 7, wherein said prosthesis is filled through a filling port disposed in said cylinder.

10. The method as recited in claim 9, wherein said fluid is injected into said pump.

11. The method as recited in claim 7, wherein there are two cylinders each installed into the penis.

12. The method as recited in claim 7, further comprising the step of deflating said reservoir before said reservoir is inserted into the pelvic cavity of the patient.

13. A method of implanting an inflatable penile prosthesis which can erect a male penis of a patient having a pelvic cavity and a scrotum, comprising the steps of:

providing a preassembled prosthesis assembly that includes:

two cylinders;

a flexible reservoir adapted to supply fluid to said cylinders;

a pump connected to said cylinders by a pair of first tubes and connected to said reservoir by a second tube, said pump being constructed to transfer fluid from said pump to said cylinders;

a fluid within said cylinders, said tubes, said pump and said reservoir, said fluid having a volume that allows said reservoir to be inserted into the pelvic cavity of the patient while said pump and said cylinders are attached to said reservoir;

inserting said reservoir into the pelvic cavity of the patient;

injecting said prosthesis assembly with fluid such that said prosthesis assembly has an operating volume of fluid; and, implanting said cylinders into the penis and said pump into the scrotum of the patient.

14. The method as recited in claim 13, wherein said cylinders have a port that allows said fluid to be injected into said cylinders.

15. The method as recited in claim 13, further comprising the step of deflating said reservoir before said reservoir is inserted into the pelvic cavity of the patient by transferring said fluid from said reservoir to said cylinders and said pump.

16. An inflatable penile prosthesis which can be implanted into a pelvic cavity, scrotum and penis of a patient, comprising:

at least one inflatable cylinder having a substantially rigid base portion and an inflatable portion;

a flexible reservoir adapted to supply fluid to said cylinder;

a pump constructed to transfer fluid from said reservoir to said cylinder;

first connecting means connecting said pump and said reservoir; and second connecting means connecting said pump and said inflatable cylinder;

a port that allows fluid to be injected therein to increase said fluid volume of said penile prosthesis to an operating volume, said port being disposed in said rigid base portion;

wherein said cylinder, said reservoir, said pump and said first and second connecting means are provided interconnected and are free of any connectors for interconnection thereof.

17. An inflatable penile prosthesis which can be implanted into a pelvic cavity, scrotum and a penis of a patient, comprising a unitary preassembled assembly comprising:

two inflatable cylinders having a substantially rigid base portion and an inflatable portion;

a flexible reservoir adapted to supply fluid to said cylinders;

a pump connected to said cylinders by a pair of first tubes and connected to said reservoir by a second tube, said pump being constructed to transfer fluid from said reservoir to said cylinders; and a filling port disposed in said prosthesis that allows fluid to be injected therein to provide said fluid volume to fill said cylinders, said pump and said reservoir to an operating volume;

said port being disposed in said rigid base portion; and wherein said cylinders, said reservoir, said pump and said first and second tubes are provided interconnected and are free of any connectors for interconnection thereof.

18. The prosthesis as recited in claim 17, wherein said cylinders have a substantially rigid base portion and an inflatable portion, and said port is disposed in said base portion.

19. A method of implanting an inflatable penile prosthesis which can erect a penis of a patient having a pelvic cavity and a scrotum, comprising the steps of:

providing a preassembled, interconnected prosthesis assembly that includes:

at least one inflatable cylinder;

a flexible reservoir adapted to supply fluid to said cylinder;

a pump connected to said cylinder and said reservoir, said pump being constructed to transfer fluid from said reservoir to said cylinder; and a filling port disposed in said prosthesis assembly that allows fluid to be injected therein to provide said fluid volume to fill said cylinders, said pump and said reservoir to an operating volume;

inserting said reservoir into the pelvic cavity of the patient;

filling said prosthesis assembly through said filling port with fluid such that said prosthesis assembly has an operating volume of fluid; and implanting said cylinder into the penis and said pump into the scrotum of the patient.

20. The method as recited in claim 19, wherein said filling port is disposed in said cylinder.

21. The method as recited in claim 19, wherein said filling port is disposed in said pump.

22. The method as recited in claim 19, wherein there are two cylinders each installed into the penis.

23. An inflatable penile prosthesis which can be implanted into a pelvic cavity, scrotum and penis of a patient, comprising:
- at least one inflatable cylinder having a rigid base portion and an inflatable portion;
- a flexible reservoir adapted to supply fluid to said cylinder;
- a pump constructed to transfer fluid from said reservoir to said cylinder;
- first connecting means connecting said pump and said reservoir;
- second connecting means connecting said pump and said inflatable cylinder;
- a fluid within said cylinder, said pump and said reservoir, said fluid having a volume that allows said reservoir to be inserted into the pelvic cavity of the patient while said pump and said cylinder are attached to said reservoir,
- a port disposed in said base portion that allows fluid to be injected therein cylinder to increase said fluid volume of said penile prosthesis to an operating volume,
- wherein said cylinder, said reservoir, said pump and said first and second connecting means are provided interconnected.

* * * * *